| United States Patent [19] | [11] 3,965,207 |
|---|---|
| Weinstein | [45] June 22, 1976 |

[54] SELECTIVE PRODUCTION OF PARA-XYLENE

[75] Inventor: Benjamin Weinstein, Morganville, N.J.

[73] Assignee: Mobil Oil Corporation, New York, N.Y.

[22] Filed: Jan. 6, 1975

[21] Appl. No.: 538,668

[52] U.S. Cl. .................... 260/671 M; 208/DIG. 2; 260/671 R; 260/671 C
[51] Int. Cl.² .................................................. C07C 3/52
[58] Field of Search ....... 260/671 R, 671 C, 671 M; 208/DIG. 2

[56] References Cited
UNITED STATES PATENTS

| 3,277,018 | 10/1966 | Plank et al. ........................ 260/671 |
|---|---|---|
| 3,367,884 | 2/1968 | Reid .............................. 208/DIG. 2 |
| 3,394,075 | 7/1968 | Smith ............................ 208/DIG. 2 |
| 3,437,587 | 4/1969 | Ellert et al. ..................... 208/DIG. 2 |
| 3,489,675 | 1/1970 | Scott ............................. 208/DIG. 2 |
| 3,527,824 | 9/1970 | Pollitzer .............................. 260/671 |
| 3,575,845 | 4/1971 | Miale ................................. 252/430 |
| 3,751,506 | 8/1973 | Burress ............................... 260/671 |

*Primary Examiner*—Delbert E. Gantz
*Assistant Examiner*—C. E. Spresser
*Attorney, Agent, or Firm*—Charles A. Huggett; Raymond W. Barclay

[57] ABSTRACT

Process for the selective production of paraxylene by methylation of toluene at a temperature between about 500°C. and about 750°C. and preferably between about 575°C. and about 700°C. in the presence of a catalyst comprising a crystalline aluminosilicate zeolite said zeolite having a silica to alumina mole ratio of at last about 12 and a constraint index, as hereinafter defined, within the approximate range of 1 to 12.

13 Claims, No Drawings

SELECTIVE PRODUCTION OF PARA-XYLENE

BACKGROUND OF THE INVENTION

1. Field of the Invention

This invention relates to a process for the selective production of para-xylene by catalytic methylation of toluene at a specified elevated temperature.

2. Description of the Prior Art

Alkylation of aromatic hydrocarbons utilizing cystalline aluminosilicate catalysts has heretofore been described. U.S. Pat. No. 2,904,697 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g. benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273–280 (1970). These workers reported selective production of para-xylene over the approximate temperature range of 200° to 275°C., with the maximum yield of para-xylene in the mixture of xylenes, i.e. about 50 percent of the xylene product mixture, being observed at 225°C. Higher temperatures were reported to result in an increase in the yield of meta-xylene and a decrease in production of para and ortho-xylenes.

While the above-noted prior art is considered of interest in connection with the subject matter of the present invention, the methylation process described herein carried out at a temperature between about 500°C. and about 750°C. utilizing a catalyst of a crystalline aluminosilicate zeolite having a silica/alumina ratio of at least about 12 and a constraint index within the approximate range of 1 to 12 to achieve unexpectedly high selective production of para-xylene has not, insofar as is known, been heretofore described. Indeed, such finding would appear to be directly contrary to expectations in light of the prior art.

Of the xylene isomers, i.e., ortho-, meta- and para-xylene, the latter is of particular value being useful in the manufacture of terephthalic acid which is an intermediate in the manufacture of synthetic fibers such as "Dacron". Mixtures of xylene isomers either alone or in further admixture with ethylbenzene, generally containing a concentration of about 24 weight percent para-xylene in the equilibrium mixture, have been previously separated by expensive superfraction and multistage refrigeration steps. Such process, as will be realized, has involved high operation costs and has a limited yield.

SUMMARY OF THE INVENTION

In accordance with the present invention, there has been discovered a process for selectively producing para-xylene in preference to meta- or ortho-xylene by reaction of toluene with a methylating agent at a temperature between about 500°C. and about 750°C. and preferably between about 575°C. and about 700°C. in the presence of a catalyst comprising a crystalline aluminosilicate zeolite said zeolite having a silica to alumina ratio of at least about 12 and a constraint index within the approximate range of 1 to 12.

In one embodiment, the catalyst is subjected to a preliminary treatment to reduce the activity thereof. Activity may be expressed in terms of a simple test in accordance with which an alpha value is determined. The alpha value reflects the selective activity of the catalyst with respect to a high activity conventional silica-alumina cracking catalyst. To determine the alpha value, n-hexane conversion is determined and converted to a rate constant per unit volume of catalyst and compared with that of silica-alumina catalyst which is normalized to a reference activity of 1000°F. Catalytic activity of the catalysts are expressed as multiple of this standard, i.e. the silica-alumina standard. The silica-alumina reference catalyst contains about 10 weight percent $Al_2O_3$ and the remainder $SiO_2$. The method of determining alpha is more fully described in the Journal of Catalysis, Vol. IV, No. 4, August, 1965, pages 527–529. The crystalline aluminosilicate zeolites utilized herein generally have an activity, in terms of alpha, of greater than 1000 and usually within the range of 1000 to 10,000. When a preliminary treatment to modify such activity is employed, the activity is reduced to less than about 500, in terms of alpha value, and preferably within the range of less than 20 but greater than zero.

Such treatment may take various forms and includes modification of the catalyst by the addition thereto of a Group VA element, such as phosphorus, antimony or arsenic; steaming of the catalyst prior to use; precoking to deposit a carbonaceous coating on the catalyst; use of a zeolite of high alkali or alkaline earth metal content or modification of the catalyst surface by contact of the zeolite with suitable compounds of nitrogen or silicon. Representative of such compounds are phenyl carbazole, dimethyl dichloro silane, trimethyl chlorosilane, hexamethyl disilozane and N-phenyl acridine. Of these various means of moderating activity, the addition of a Group VA element and particularly phosphorus to the catalyst is particularly applicable in achieving high selective production of para-xylene under the temperature conditions employed herein.

In another embodiment, the catalyst comprising a crystalline aluminosilicate zeolite, as above characterized, and in the hydrogen or acid form is utilized under temperature conditions within the preferred range of about 575°C. to about 700°C. The catalyst, under such circumstances, may be used as such or in combination with a porous matrix or diluent material of lesser activity, e.g. silica gel.

In addition to the use of temperatures within the specified range, high weight hourly space velocities greater than about 1 weight of charge per weight of catalyst per hour have been found to increase the selectivity of paraxylene production in the toluene methylation reaction of interest. It is contemplated that a weight hourly space velocity as high as 2000 weight of charge per weight of zeolite catalyst component per hour may feasibly be employed. Preferably, the weight hourly space velocity utilized herein is within the approximate range of 5 to 1500 weight of charge per weight of catalyst per hour.

Without being limited by any theory, it would appear that the high selectivity for para-xylene achieved in the present process is attributable, at least in part, to the use of temperatures where alkylation of toluene with a methylating agent is favored over isomerization of the initially formed para- and ortho-xylenes to meta-xylene, coupled with rapid removal from the reaction zone of the initially formed products, by use of high weight hourly space velocities, before substantial isomerization of such products takes place. Thus, in the alkylation of toluene with methanol, substitution of the methyl group of toluene is para/ortho orientation and the first stage reaction products are considered to be para and ortho isomers. However, since (1) such alkylation and (2) isomerization of the initially formed products occur successively or almost simultaneously, an overall product ordinarily results which corresponds closely to the thermodynamic equilibrium xylene mixture in which the para:meta:ortho ratio is approximately 1:2:1. Under the conditions employed in the present process, a xylene product may be achieved in which para-xylene approaches 100 percent. The improved para-xylene yield reduces the cost of production and most important the cost of separation of para-xylene from its isomer which is the most expensive step in the current method employed for producing para-xylene.

DESCRIPTION OF THE SPECIFIC EMBODIMENTS

The zeolite catalysts herein described are members of a novel class of zeolites exhibiting some unusual properties. These catalysts induce profound transformations of aliphatic hydrocarbons to aromatic hydrocarbns in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conductive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000°F. for at least 15 minutes. The catalyst is then flushed with helium and the temperature adjusted between 550°F. and 950°F. to give an overall conversion between 10 and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
| --- | --- |
| ZSM-5 | 8.3 |
| ZSM-11 | 8.7 |
| ZSM-12 | 2 |
| ZSM-21 | 4.5 |
| ZSM-35 | 4.5 |

-continued

| CAS | C.I. |
|---|---|
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° to 950°F., with accompanying conversion between 10 and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° to 950°F., the constraint index will have a value for any given zeolite of interest herein within the approximate range of 1 to 12.

The class of zeolites defined herein is exemplified by ZSM-5, ZSM-11, ZSM-12, ZSM-21, ZSM-35 and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-21 is more particularly described in U.S. application Ser. No. 560,142, filed Mar. 20, 1975. This zeolite can be identified, in terms of mole ratios of oxides and in the anhydrous state, as follows:

$(0.3-2.5)R_2O : (0-0.8)M_2O : Al_2O_3 : > 8 SiO_2$ wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$(0.4-2.5)R_2O : (0-0.6) M_2Al_2O_3 : xSiO_2$ wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to about 50.

The synthetic ZSM-21 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | weak |
| 2.66 ± 0.05 | weak |
| 2.60 ± 0.05 | Weak |
| 2.49 ± 0.05 | Weak |

A further characteristic of ZSM-21 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-21 (after calcination at 600°C) is less than 10, whereas that ratio for the natural ferrierite is substantially greater than 10, for example, as high as 34 or higher.

Zeolite ZSM-21 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R++M+ OH⁻/SiO₂ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90°C. to about 400°C. for a period of time of from about 6 hours to about 100 days. A more preferred temperature range is from about 150°C. to about 400°C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230°F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0.0.6)\ M_2O : Al_2O_3 : xSiO_2$$

wherein R is an organic nitrogen-containing cation derived from ethylenediamine or pyrrolidine, M is an alkali metal, especially sodium, and $x$ is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong - Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600°C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90°C. to about 400°C. for a period of time of from about 6 hours to about 100 days. A more preferred temperature range is from about 150°C. to about 400°C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230°F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000°F. for 1 hour, for example, followed by base exchange with ammonium salts followed by calcination at 1000°F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000°F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-21 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumonite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form the zeolite is conveniently converted to the hydrogen form generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, calcium, nickel, zinc or rare earth metals.

The crystals of zeolite in a form substantially free of alkali metal, i.e. containing less than about 1.5 weight percent alkali metal, may either be employed as such or in combination with a porous matrix or diluent. The zeolite may, as noted hereinabove, be modified by suitable treatment to reduce the activity thereof prior to use in the toluene methylation reaction of interest.

Suitable modifying treatments include contacting of the zeolite with compounds of nitrogen or silicon. Such manner of modification is more particularly described in application Ser. No. 509,188 filed Sept. 25, 1974, the entire contents of which are incorporated herein by reference.

Another suitable modifying treatment involves the addition to the catalyst of a Group VA element, e.g. phosphorus, antimony or arsenic in an amount of at least about 0.5 weight percent. Such method of catalyst treatment is more particularly described in application Ser. No. 538,666 filed of even date herewith, the entire contents of which are incorporated herein by reference.

Still another modifying treatment entails steaming of the catalyst by contact with an atmosphere containing from about 5 to about 100 percent steam at a temperature of from about 250° to about 1000°C. and under pressures ranging from sub-atmospheric to several hundred atmospheres to reduce the alpha value thereof to less than 500 and preferably less approximate than 20 but greater than zero. Such method of catalyst treatment is more particularly described in application Ser. No. 538,665 filed of even date herewith, the entire contents of which are incorporated herein by reference.

Another modifying treatment involves precoking of the catalyst to deposit a coating of between about 3 and about 75 weight percent of coke thereon. This method of catalyst treatment is more particularly described in application Ser. No. 538,664 filed of even date herewith, the entire contents of which are incorporated herein by reference.

Prior to use, the above-described zeolite catalyst is calcined in an inert atmosphere, e.g. helium or in an oxygen-containing atmosphere, e.g. air. Calcination takes place at a temperature in the approximate range of 500° to 700°C. and preferably between 450° and 550°C.

In practicing the desired methylation process it may be desirable to incorporate the zeolite in another material resistant to the temperature and other conditions employed in the methylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

Methylation of toluene in the presence of the above-described catalyst is effected by contact of the toluene with a methylating agent, preferably methanol, at a temperature between about 500°C. and about 750°C. and preferably between about 575°C. and about 700°C. At the higher temperatures, the zeolites of high silica/alumina ratio are preferred. For example, ZSM-5 of 300 $SiO_2/Al_2O_3$ ratio and upwards is very stable at high temperatures. The reaction generally takes place at atmospheric pressure, but the pressure may be within the approximate range of 1 atmosphere to 1000 psig. The molar ratio of methylating agent to toluene is generally between about 0.05 and about 5. When methanol is employed as the methylating agent a suitable molar ratio of methanol to toluene has been found to be approximately 0.1-2 moles of methanol per mole of toluene. With the use of other methylating agents such as methylchloride, methylbromide, dimethylether or dimethylsulfide, the molar ratio of methylating agent to toluene may vary within the aforenoted range. Reaction is suitably accomplished utilizing a weight hourly space velocity as above defined, of between about 1 and about 2000 and preferably between about 5 and about 1500. The reaction product consisting predominantly of para-xylene, together with comparatively smaller amounts, if any, of meta-xylene and ortho-xylene may be separated by any suitable means, such as by passing the same through a water condenser and subsequently passing the organic phase through a column in which chromatographic separation of the xylene isomers is accomplished.

The process of this invention may be carried out as a batch type, semi-continuous or continuous operation utilizing a fixed or moving bed catalyst system. Multiple injection of the methylating agent, e.g. methanol, may suitably be employed. A preferred embodiment entails use of a fluidized catalyst zone wherein the reactants, i.e. toluene and methylating agent are passed concurrently or countercurrently through a moving fluidized bed of the catalyst. The fluidized catalyst after use is conducted to a regeneration zone wherein accumulated coke is removed by combustion.

The following examples will serve to illustrate the process of this invention without limiting the same:

EXAMPLE 1

ZSM-5 crystals were obtained using the following reactants:
Silicate Solution
42.2 lb. Q-Brand Sodium Silicate ($Na_2O/SiO_2 = 3.3$)
52.8 lb. Water
Acid Solution
612 grams Aluminum Sulfate
1600 grams Sulfuric Acid
7190 grams Sodium Chloride
72.2 lb. Water
Organics
1290 grams Tri-n-proplame
1110 grams n-Propylbromide The silicate solution and acid solution were nozzle mixed to form a gelatinous precipitate that was charged to a 30 gallon stirred autoclave. When gelation was complete the organics were added and the temperature raised to 315°F. with agitation. The reaction mixture was held at 315°F with an agitation rate of 121 RPM for 17 hours. The product at this time was analyzed by X-ray diffraction and was reported to be ZSM-5. The product was then washed free of soluble salts and dried. Analysis of the product gave the following in terms of mole ratios:

| | |
|---|---|
| $Al_2O_3$ | 1.0 |
| $SiO_2$ | 74.4 |
| $Na_2O$ | 0.31 |
| N | 2.26 |
| C | 21.9 |

The ZSM-5 so prepared was precalcined in air at 370°C. and thereafter ammonium exchanged by contacting twice with 5N $NH_4Cl$ solution at 100°C. (15 ml. per gram zeolite), once for 16 hours, the second time for 4 hours, filtered, washed free of chloride and air dried.

The resulting ammonium form of ZSM-5 was converted to the hydrogen form by calcination in air at 1°C./minute to 538°C. and then held at 538°C. for 10 hours.

EXAMPLE 2

Five grams of pelleted HZSM-5 prepared as in Example 1 and 75 ml. of toluene were heated to reflux under a water condenser. There was no stirring, so as to avoid shattering the pellets, and a slow stream of nitrogen was bubbled through the solution to minimize bumping. After 45 minutes, the mixture was cooled to room temperature and 4 grams of diphenyl phosphine chloride were added. The resulting mixture was refluxed for 16 hours. The solvent was then removed by distilling to dryness. The resulting solids were then calcined in air at 500°C. for 1 hour.

EXAMPLES 3-7

Toluene and methanol in a molar ratio mixture of 2 (toluene/methanol) were passed over 3 grams of the catalyst modified as in Example 2 at a weight hourly space velocity of 9 at various temperatures. The conditions and results are shown in Table I below.

TABLE I

| Example | Temp °C | Percent Xylenes in Aromatic Products | Percent Para-Xylene In Xylene Product |
|---|---|---|---|
| 3 | 400 | 86 | 64 |
| 4 | 450 | 89 | 74 |
| 5 | 500 | 91 | 79 |
| 6 | 550 | 91 | 83 |
| 7 | 600 | 93 | 81 |

From the above table, it will be seen that selectivity for para-xylene increased at the higher temperatures with an enhanced yield of para-xylene being obtained at temperatures of 500°C. and above.

EXAMPLES 8–13

Toluene and methanol in a molar ratio mixture of 1 and 2 were passed over 3 grams of the catalyst modified as in Example 2 at temperatures of 550°C. and 600°C. at varying weight hourly space velocities. The conditions and results are shown in Table II below.

TABLE II

| Example | Temp. °C | WHSV | Toluene/Methanol | Percent Xylenes in Aromatic Products | Percent Para-Xylene In Xylene Product |
|---|---|---|---|---|---|
| 8 | 550 | 4.4 | 1 | 86 | 71 |
| 9 | 550 | 9.8 | 1 | 87 | 81 |
| 10 | 550 | 22.2 | 1 | 86 | 83 |
| 11 | 600 | 8.4 | 2 | 93 | 81 |
| 12 | 600 | 17.0 | 2 | 92 | 86 |
| 13 | 600 | 35.9 | 2 | 93 | 88 |

From the above table, it will be evident that higher space velocity at the temperatures utilized herein lead to increased selectivity to para-xylene.

EXAMPLES 14–20

Toluene and methanol in a molar ratio of 1:1 were passed over 2 grams of catalyst prepared in a manner similar to that of Example 1 which had been contacted with 100 percent steam at 870°C. for 6 hours. The catalyst was calcined at 550°C. for 1 hour before each run.

Reaction of toluene and methanol was accomplished at temperatures of from 550° to 700°C. at weight hourly space velocities between 11.4 and 24.2. A reaction product characterized by a high content of xylene was obtained in each instance, with selective production of para-xylene. The results are set forth in Table III below.

TABLE III

| Ex. | Temp °C | WHSV | Conversion, % Toluene | Conversion, % MeOH | Xylenes p:m:o | Wt.% Xylene in Aromatic Products |
|---|---|---|---|---|---|---|
| 14 | 550 | 11.8 | 15 | 75 | 63/20/17 | 88 |
| 15 | 600 | 11.4 | 25 | 79 | 66/20/15 | 86 |
| 16 | 600 | 24.1 | 15 | 73 | 68/18/14 | 90 |
| 17 | 650 | 11.8 | 36 | 90 | 67/20/13 | 86 |
| 18 | 650 | 24.1 | 23 | 78 | 72/16/11 | 89 |
| 19 | 700 | 11.8 | 44 | 95 | 70/19/11 | 86 |
| 20 | 700 | 24.2 | 33 | 95 | 77/14/9 | 85 |

From the above table, it will be evident that over the temperature range of 550° to 700°C. at the same space velocity, selectivity to para-xylene increased with increasing temperature.

EXAMPLES 21–31

A catalyst of 5% HZSM-5 and 95% SiO₂ was prepared by blending 5 percent by weight HZSM-5 powder and 95 percent by weight silica gel of 200 mesh average particle size, pressing into wafers and sizing to 8–14 mesh.

A 1/1 molar ratio mixture of toluene and methanol was contacted with 2 grams of the above catalyst under the reaction conditions and with the results shown in Table IV. below

TABLE IV*

| Ex. | Time on Stream | Temp °C | WHSV | Conversion, % Toluene | Conversion, % Methanol | Wt. % Xylenes in Aromatic Products | Xylene Ratio Para | Xylene Ratio Meta | Xylene Ratio Ortho |
|---|---|---|---|---|---|---|---|---|---|
| 21 | 0.5 | 550 | 198 | 31 | 81 | 82 | 50 | 30 | 20 |
| 22 | 2.0 | 650 | 790 | 25 | 73 | 85 | 76 | 16 | 8 |
| 23 | 2.5 | 600 | 776 | 8 | 56 | 89 | 87 | 8 | 5 |
| 24 | 3.5 | 650 | 1155 | 14 | 55 | 90 | 90 | 7 | 3 |
| 25 | 4.0 | 650 | 496 | 18 | 77 | 85 | 88 | 8 | 4 |
| 26 | 4.8 | 550 | 196 | 33 | 86 | 84 | 70 | 19 | 10 |
| 27 | 5.5 | 650 | 800 | 19 | 64 | 88 | 86 | 9 | 5 |
| 28 | 7.0 | 650 | 196 | 31 | 85 | 81 | 80 | 13 | 7 |
| 29 | 32.5 | 550** | 250 | 1 | 11 | 50 | 100 | 0 | 0 |
| 30 | 33.3 | 550 | 176 | 29 | 77 | 86 | 72 | 18 | 11 |
| 31 | 34.5 | 650 | 813 | 21 | 60 | 89 | 86 | 9 | 5 |

*Catalyst was calcined at 550°C. for 1 hour before each run except between the runs of Examples (29) and (30) and (30) and (31) where calcination was at 600°C. for 1 hour.

**Prior to this run, toluene-methanol feed was passed over the catalyst for 25.5 continuous hours. No calcination was carried out before this run.

The results shown in the above table illustrate that at high temperatures and high space velocities, the ZSM-5 catalyzed alkylation of toluene with methanol produces para-xylene in high selectivity. It will be further evident that the catalyst had a break-in period where activity remained approximately constant, but para-xylene selectivity increased. This is shown by comparison of the runs of Examples 21 and 26 at 550°C., where para-xylene selectivity increased from 50 percent to 70 percent at constant conversion and the runs of Examples 22 and 27 at 650°C. where para-xylene selectivity increased from 76 percent to 86 percent. The improved selectivities of Examples 26 and 27 remained the same after the catalyst was run for 25 continuous hours and regenerated in air at 600°C. During the 25 hours of continuous stream time between the runs of Examples 28 and 29, catalyst activity fell to approximately zero.

Air regeneration at 600°C. for 1 hour restored catalyst activity and selectivity to their pre-aging levels.

EXAMPLE 32

A catalyst was prepared by blending 5 weight percent HZSM-5 and 95 weight percent silica gel.

Toluene and methanol in a 1:1 molar ratio were passed over this catalyst at a temperature of 550°C at a weight hourly space velocity of 250. Methanol conversion was 11 weight percent. The xylene content in the aromatics product amounted to 50 weight percent. After 32.5 hours on stream, the catalyst had deactivated considerably due to the accumulation of coke thereon and produced 100 percent selectivity to para-xylene at about 1 percent toluene conversion.

EXAMPLE 33

A catalyst was prepared by blending 5 weight percent HZSM-5 extrudate (containing 65 wt. percent HZSM-5 and 35 wt. percent $Al_2O_3$ binder) and 95 weight percent silica gel.

Toluene and methanol in a 1:1 molar ratio were passed over this catalyst at a temperature of 550°C at a weight hourly space velocity of 241. Methanol conversion was 10 weight percent. The xylene content in the aromatics product was 100 weight percent. After 4.5 hours on stream the catalyst had deactivated considerably due to the accumulation of coke thereon and gave 100 percent selectivity to para-xylene at about 1 percent toluene conversion.

EXAMPLES 34-35

Three grams of HZSM-5 and 45 ml. of toluene were refluxed for 1 hour, cooled and then 1.14 grams of trimethylphosphate were added. The resulting mixture was refluxed overnight, evaporated to dryness and thereafter calcined for 1 hour at 500°C. The catalyst so prepared contained 4.06 weight percent phosphorus.

Toluene and methanol in a molar ratio of 1 were contacted with 2 grams of the above catalyst. The reaction conditions and results are shown below in Table V.

TABLE V

| Ex. | Temp °C | WHSV | Conversion, % Toluene | Conversion, % Methanol | Wt % Xylenes in Aromatic Products | Para | Xylenes Meta | Ortho |
|---|---|---|---|---|---|---|---|---|
| 34 | 550 | 12.1 | 17 | 87 | 82 | 86 | 8 | 7 |
| 35 | 600 | 24.1 | 16 | 80 | 92 | 98 | 2 | 0 |

EXAMPLES 36-38

Three grams of HZSM-5 and 45 ml. of toluene were refluxed for 1 hour, cooled and then 1.14 grams of trimethylphosphate were added. The resulting composite was evaporated to dryness and thereafter calcined for 1 hour at 500°C. The catalyst so prepared contained 2.39 weight percent phosphorous.

Toluene and methanol in a molar ratio of 1 were contacted with 2 grams of the above catalyst. The reaction conditions and results are shown below in Table VI.

TABLE VI

| Ex. | Temp °C | WHSV | Conversion, % Toluene | Conversion, % Methanol | Wt % Xylenes in Aromatic Products | Para | Xylenes Meta | Ortho |
|---|---|---|---|---|---|---|---|---|
| 36 | 550 | 19.5 | 42 | 95 | 84 | 73 | 19 | 9 |
| 37 | 600 | 20.8 | 44 | 96 | 84 | 74 | 18 | 8 |
| 38 | 600 | 44.0 | 39 | 89 | 85 | 80 | 14 | 7 |

Comparing the above results shown in Tables V and VI, it will be evident that higher para-xylene selectivities were observed at the higher temperatures, higher phosphorus content and lower conversions.

EXAMPLES 39-46

Sixty seven grams of dried HZSM-5 were combined with 26.5 grams of trimethylphosphite, $(CH_3O)_3 P$ and 235 ml. of octane in a flask. The mixture was gently refluxed for 18 hours. A dry nitrogen purge was used. After cooling, the catalyst was filtered and washed with 500 ml. of methylene chloride followed by 500 ml. of pentane. The catalyst was then calcined in air at 150 ml./min. for 16 hours at a temperature of 500°C. Analysis indicated a phosphorus content of 3.45 percent by weight.

Toluene was alkylated with methanol under various conditions of reaction with this catalyst. The conditions employed and resulting conversions are shown in Table VII below.

TABLE VII

| Example | 39 | 40 | 41 | 42 | 43 | 44 | 45 | 46 |
|---|---|---|---|---|---|---|---|---|
| Temp °C | 550 | 550 | 550 | 400 | 600 | 600 | 600 | 600 |
| WHSV | 10.4 | 10.4 | 10.4 | 10.4 | 10.4 | 21.9 | 44.6 | 74.0 |
| Toluene/Methanol (Molar Feed Ratio) | 1 | 1 | 1 | 1 | 1 | 1 | 1 | 1 |
| Stream Time (Hrs.) | 1 | 2 | 3 | 4 | 5 | 6 | 7 | 8 |
| Conv. Toluene, Wt.% | 42.5 | 42.3 | 43.7 | 15.6 | 47.9 | 46.5 | 34.2 | 25.8 |
| Conv. Methanol, Wt.% | 96.5 | 95.4 | 94.4 | 83.0 | 96.8 | 93.6 | 82.8 | 72.8 |
| Xylenes in Aromatic Prod. Wt. % | 75.2 | 76.9 | 78.4 | 81.2 | 81.9 | 84.0 | 86.8 | 89.4 |
| % Paraxylenes in Xylenes | 54.8 | 56.2 | 57.7 | 42.5 | 59.9 | 74.2 | 80.7 | 83.2 |

It will be evident from the above results that selectivity for para-xylene increased significantly at higher temperature and space velocity.

EXAMPLES 47–55

Four of HZSM-5, 0.75 gram of 85% phosphoric acid ($H_3PO_4$) and 150 ml. of methanol were combined and refluxed gently for 16 hours with a nitrogen purge. The solvent was removed by distillation and the remaining catalyst heated to 250°C. in air. The catalyst was then placed in a furnace at 500°C. in air for 1 hour. Elemental analysis showed a phosphorus content of 4.45 weight percent.

Toluene was alkylated with methanol under various conditions of reaction with this catalyst. The conditions used and the resulting conversions are shown in Table VIII below.

TABLE VIII

| Example | 47 | 48 | 49 | 50 | 51 | 52 | 53 | 54 | 55 |
|---|---|---|---|---|---|---|---|---|---|
| Temp °C | 550 | 550 | 550 | 550 | 400 | 600 | 600 | 600 | 600 |
| WHSV | 10.4 | 10.4 | 10.4 | 10.4 | 10.4 | 10.5 | 16.8 | 21.9 | 42.2 |
| Toluene/Methanol (Molar Feed Ratio) | 1 | 1 | 1 | 1 | 1 | 1 | 1 | 1 | 1 |
| Stream Time (Hrs.) | 1 | 2 | 3 | 9 | 4 | 5 | 6 | 7 | 8 |
| Conv. Toluene, Wt.% | 37.7 | 35.6 | 34.9 | 31.0 | 11.2 | 39.3 | 36.6 | 35.7 | 24.2 |
| Conv. Methanol, Wt.% | 95.8 | 93.9 | 92.5 | 95.0 | 77.0 | 92.4 | 91.0 | 88.7 | 71.9 |
| Xylenes in Aromatic Prod. Wt.% | 73.6 | 77.2 | 80.4 | 87.6 | 80.9 | 82.8 | 87.0 | 88.4 | 90.7 |
| % Paraxylene in Xylenes | 57.8 | 64.4 | 69.2 | 84.6 | 50.7 | 73.2 | 84.0 | 87.3 | 90.7 |

From the above results, it will be seen again that the selectivity for para-xylene increased significantly at higher temperature and space velocity.

It is to be understood that the foregoing description is merely illustrative of preferred embodiments of the invention of which many variations may be made by those skilled in the art within the scope of the following claims without departing from the spirit thereof.

I claim:

1. A process for the selective production of para-xylene which comprises reacting toluene with a methylating agent at a temperature between about 575°C and about 750°C in the presence of a catalyst comprising a crystalline aluminosilicate zeolite, said zeolite having a silica to alumina ratio of at least about 12 and a constraint index within the approximate range of 1 to 12.

2. The process of claim 1 wherein said methylating agent is methanol.

3. The process of claim 2 wherein the molar ratio of methanol to toluene is between about 0.1 and about 2.

4. The process of claim 1 wherein said reacting takes place at a weight hourly space velocity of between about 5 and about 1500.

5. A process for the selective production of paraxylene which comprises reacting toluene with a methylating agent at a temperature between about 575°C. and about 700°C. in the presence of a catalyst comprising a crystalline aluminosilicate zeolite said zeolite having a silica to alumina ratio of at least about 12 and a constraint index within the approximate range of 1 to 12.

6. The process of claim 5 wherein said crystalline aluminosilicate zeolite is characterized by a silica/alumina ratio in excess of 30.

7. The process of claim 5 wherein said zeolite is ZSM-5.

8. The process of claim 5 wherein said methylating agent is methanol, methylchloride, methylbromide, dimethylether or dimethylsulfide.

9. The process of claim 5 wherein said reacting takes place at a weight hourly space velocity of between about 1 and about 2000.

10. The process of claim 5 wherein said crystalline aluminosilicate zeolite is in the hydrogen form.

11. The process of claim 5 wherein said crystalline aluminosilicate zeolite is used in combination with a porous matrix.

12. The process of claim 11 wherein said matrix is silica gel.

13. The process of claim 5 wherein the molar ratio of methylating agent to toluene is between about 0.05 and about 5.

* * * * *

UNITED STATES PATENT AND TRADEMARK OFFICE
CERTIFICATE OF CORRECTION

PATENT NO. : 3,965,207
DATED : June 22, 1976
INVENTOR(S) : BENJAMIN WEINSTEIN

It is certified that error appears in the above-identified patent and that said Letters Patent are hereby corrected as shown below:

Column 5, line 62, in the equation: "$M_2Al_2O_3$" should be --$M_2O : Al_2O_3$--.

Column 12, line 63, Table I, Example 7, under heading Percent Xylenes in Aromatic Products last number should be --93--, figure 81 belongs in last column.

Column 17, line 6, after "Four", add --(4) grams--.

Signed and Sealed this

Twenty-first Day of September 1976

[SEAL]

Attest:

RUTH C. MASON
*Attesting Officer*

C. MARSHALL DANN
*Commissioner of Patents and Trademarks*